United States Patent
Notelivitz et al.

(10) Patent No.: US 6,524,616 B1
(45) Date of Patent: Feb. 25, 2003

(54) COMPOSITIONS AND METHODS FOR TREATING OR PREVENTING NEURODEGENERATION AND COGNITIVE DECLINE AND DYSFUNCTION ASSOCIATED WITH ALZHEIMER'S DISEASE, AGING, OTHER DEMENTIA RELATED DISORDERS AND ESTROGEN DEFICIENCY RELATED CONDITIONS

(75) Inventors: Morris Notelivitz, Gainesville, FL (US); Thomas B. Clarkson, Clemmons, NC (US); Yuanlong Pan, Winston-Salem, NC (US); Mary S. Anthony, Clemmons, NC (US)

(73) Assignees: Wake Forest University Health Services, Winston-Salem, NC (US); Morris Notelovitz, Gainesville, FL (US)

( * ) Notice: Subject to any disclaimer, the term of this patent is extended or adjusted under 35 U.S.C. 154(b) by 0 days.

(21) Appl. No.: 09/602,513

(22) Filed: Jun. 23, 2000

Related U.S. Application Data

(60) Provisional application No. 60/141,189, filed on Jun. 25, 1999.

(51) Int. Cl.[7] .................................................. A61K 9/20
(52) U.S. Cl. ...................................... 424/464; 424/757
(58) Field of Search ................................ 424/401, 464, 424/757

(56) References Cited

U.S. PATENT DOCUMENTS 5,952,374 A * 9/1999 Clarkson, Jr. et al. ...... 514/456
6,036,973 A * 3/2000 Guttard et al. .............. 424/457

OTHER PUBLICATIONS

Anthony, Mary S. et al., "Soy Protein Versus Soy Phytoestrogens in the Prevention of Diet–Induced Coronary Artery Atherosclerosis of Male Cynomolgus Monkeys," *Arterio. Thrombo. Vasc. Biol.* 17:2524 (1997).

Bartus, Raymond T. et al., "The Cholinergic Hypothesis of Geriatric Memory Dysfunction," *Science* 217:408 (1982).

Bergkvist, Leif et al., "Hormone Replacement Therapy and Breast Cancer," *Drug Safety* 15:360 (1996).

Brown, Myles, "Estrogen Receptor Molecular Biology," *Breast Cancer* 8:101 (1994).

Cavicchioli, Lucio et al., "Choline Acetyltransferase Messenger RNA Expression in Developing and Adult Rat Brain: Regulation by Nerve Growth Factor," *Mol. Brain Res.* 9:319 (1991).

Clarkson, Thomas B. et al., "Estrogenic Soybean Isoflavones and Chronic Disease—Risks and Benefits," *Trends Endocrinol. Metab.* 6:11 (1995).

Clarkson, Thomas B. et al., "Hormone Replacement Therapy and Coronary Artery Atherosclerosis: the Monkey Model," *Brit. J. Obstet. Gynaecol.* 103:53 (1996).

Ettinger, Bruce, "Prevention of Osteoporosis: Treatment of Estradiol Deficiency," *Obstet. & Gynecol.* 72:12S (1988).

(List continued on next page.)

Primary Examiner—Jose' G. Dees
Assistant Examiner—Konata M George
(74) Attorney, Agent, or Firm—Kilpatrick Stockton LLP

(57) ABSTRACT

A composition for improving memory and concentration in mammals with disorders associated with memory impairment. The composition comprises a combination of at least one phytoestrogen and at least one acetylcholinesterase inhibitor such as Huperzine A, or any derivative, analog, metabolite or combination thereof. The composition may further include at least one mammalian estrogen. The method of the invention comprises the co-administration of at least one phytoestrogen and at least one acetylcholinesterase inhibitor in a therapeutically effective amount. Additionally, a mammalian estrogen may be co-administered.

8 Claims, 8 Drawing Sheets

Huperzine-A

OTHER PUBLICATIONS

Evans, Denis A. et al., "Prevalence of Alzheimer's Disease in a Community Population of Older Persons—Higher Than Previously Reported," *JAMA* 262:2251 (1989).

Foth, Dolores et al., "Effects of Mammalian and Plant Estrogens on Mammary Glands and Uteri of Macaques," *Am. J. Clin. Nutr.* 68:1413S (1998).

Francis, Paul T. et al., "Neurochemical Studies of EarlyOnset Alzheimer's Disease—Possible Influence on Treatment," *New England Journal of Medicine* 313:7–11 (Jul. 4, 1985).

Gibbs, Robert B. et al., "Effects of Estrogen Replacement on the Relative Levels of Choline Acetyltransferase, trkA, and Nerve Growth Factor Messenger RNAs in the Basal Forebrain and Hippocampal Formation of Adult Rats," *Exp. Neurol.* 129:70 (1994).

Graves, A. B. et al., "Prevalence of Dementia and Its Subtypes in the Japanese American Population of King County, Washington State—The Kame Project," *Am. J. Epidemiol.* 144:760 (1996).

Green, Stephen et al., "Human Oestrogen Receptor cDNA: Sequence, Expression and Homology to v–erb–A," *Nature* 320:134 (1986).

Hallak, Marta et al., "Relation of Brain Regional Physostigmine Concentration to Cholinesterase Activity and Acetylcholine and Choline Levels in Rat," *Neurochem. Res.* 11:1037 (1986).

Ishii, Kayoko et al., "Complementary DNAs for Choline Acetyltransferase from Spinal Cords of Rat and Mouse: Nucleotide Sequences, Expression in Mammalian Cells, and in Situ Hybridization," *Mol. Brain Res.* 7:151 (1990).

Jorm, A. F. et al., "The Prevalence of Dementia: A Quantitative Integration of the Literature," *Acta Psychiatr. Scand.* 76:465 (1987).

King, Roger A. et al., "Absorption and Excretion of the Soy Isoflavone Genistein in Rats," *J. Nutr* 176 (1996).

Knopp, Robert H., "The Effects of Postmenopausal Estrogen Therapy on the Incidence of Arteriosclerotic Vascular Disease," *Obstet. Gynecol.* 72:23S (21998).

Kosik, Kenneth S., "Alzheimer's Disease: A Cell Biological Perspective," *Science* 256:780 (1992).

Kuiper, George G. J. M. et al., "Cloning of a Novel Estrogen Receptor Expressed in Rat Prostate and Ovary," *Proc. Natl. Aca. Sci. USA* 93:5925 (1996).

Kuiper, George G. J. M. et al., "Comparison of the Ligand Binding Specificity and Transcript Tissue Distribution of Estrogen Receptors α and β," *Endocrinol.* 138:863 (1997).

Laganiére, S. et al., "Acute and Chronic Studies with the Anticholinesterase Huperzine A: Effect on Central Nervous System Cholinergic Parameters," *Neuropharmacol.* 30:763 (1991).

Lauterborn, Julie C. et al., "In Situ Hybridization Localization of Choline Acetyltransferase mRNA in Adult Rat Brain and Spinal Cord," *Mol. Brain Res.* 17:59 (1993).

Levi, Fabio et al., "Oestrogen Replacement Treatment and the Risk of Endometrial Cancer: an Assessment of the Role of Covariates," *Eur. J. Cancer* 29A:1445 (1993).

Liu, Jia–Sun et al., "The Structures of Huperzine A and B, Two New Alkaloids Exhibiting Marked Anticholinesterase Activity," *Can. J. Chem.* 64:837 (1986).

Luine, Victoria N., "Estradiol Increases Choline Acetyltransferase Activity in Specific Basal Forebrain Nuclei and Projection Areas of Female Rats," *Exp. Neurol.* 89:484 (1985).

Mosselman, Sietse et al., "Erβ: Identification and Characterization of a Novel Human Estrogen Receptor," *FEBS* 392:49 (1996).

Paganini–Hill, A., "Oestrogen Replacement Therapy and Alzheimer's Disease," *Brit. J. Obstet.* 103:80 (1996).

Pan, Yuanlong et al., "Effect of Estradiol and Soy Phytoestrogens on Choline Acetyltransferase and Nerve Growth Factor mRNAs in the Frontal Cortex and Hippocampus of Female Rats," *Proc. Soc. Exp. Biol. Med.* 221(2):118 (1999).

Pan, Yuanlong et al., "Evidence for Up–Regulation of Brain-Derived Neurotrophic Factor mRNA by Soy Phytoestrogens in the Frontal Cortex of Retired Breeder Female Rats," *Neurosci, Lett.* 261 (1–2):17 (1999).

Pan, Yuanlong et al., "Expression of Ceruloplasmin Gene in Human and Rat Lymphocytes," *Biochem. Biophy. Acta* 1307:233 (1996).

Ruiz–Larrea, M. Begoña et al., "Antioxidant Activity of Phytoestrogenic Isoflavones," *Free Rad. Res.* 26:63 (1997).

Sfakianos, Jeff et al., "Intestinal Uptake and Biliary Excretion of the Isoflavone Genistein in Rats," *J. Nutr.* 127:1260 (1997).

Sherwin, Barbara B., "Estrogenic Effects on Memory in Women," *Ann. NY Acad. Sci.* 743:213 (1994).

Simpkins, James W. et al., "The Potential Role for Estrogen Replacement Therapy in the Treatment of the Cognitive Decline and Neurodegeneration Associated with Alzheimer's Disease," *Neurobiol. Aging* 15:s195 (1994).

Singh, Meharvan et al., "The Effect of Ovariectomy and Estradiol Replacement on Brain–Derived Neurotrophic Factor Messenger Ribonucleic Acid Expression in Cortical and Hippocampal Brain Regions of Female Sprague–Dawley Rats," *Endocrinol.* 136:2320 (1995).

Singh, Meharvan et al., "Ovarian Steroid Deprivation Results in a Reversible Learning Impairment and Compromised Cholinergic Function in Female Sprague–Dawley Rats," *Brain Research* 644:305 (1994).

Singh, Meharvan, "Ovariectomy Reduces chAT Activity and NFG mRNA Levels in the Frontal Cortex and Hippocampus of the Female Sprague–Dawley Rat" *Abstr. Soc. Neurosci* 19:1254 (1993).

Skolnick, Andrew A., "Old Chinese Herbal Medicine Used for Fever Yields Possible New Alzheimer Disease Therapy," *JAMA* 227:776 (1997).

Sohrabji, Farida et al., "Identification of a Putative Estrtogen Response Element in the Gene Encoding Brain–Derived Neurotrophic Factor," *Proc. Nat'l. Acad. Sci. USA I* 92:11110 (1995).

Speroff, Leon et al., "The Comparative Effect on Bone Density, Endometrium, and Lipids of Continuous Hormones as Replacement Therapy (CHART Study)—A Randomized Controlled Trial," *JAMA* 276:1397 (1996).

Stehbens, W. E., "The Quality of Epidemiological Data in Coronary Heart Disease and Atherosclerosis," *J. Clin. Epidemiol* 46: 1337–1346 (1993).

Strauss, S. et al., "Increased Levels of Nerve Growth Factor (NGF) Protein and mRNA and Reactive Gliosis Following Kainic Acid Injection into the Rat Striatum," *Neurosci. Lett.* 168:193 (1994).

Sullivan, J. M., "Hormone Replacement Therapy and Cardiovascular Disease: the Human Model," *Brit. J. Obstet. Gynaecol.* 103:59 (1996).

Tang, Ming–Xin et al., "Effect of Oestrogen During Menopause on Risk and Age at Onset of Alzheimer's Disease," *Lancet* 348:429 (1996).

Tang, X.-C. et al., "Effect of Huperzine A, a New Cholinesterase Inhibitor, on the Central Cholinergic System of the Rat," *Neurosci. Res.* 24.276 (1989).

Tang, Xi-Can, "Huperzine A (Shuangyiping): A Promising Drug for Alzheimer's Disease," *Acta Pharmacol. Sinica.* 17:481 (1996).

Watkins, Paul B. et al., "Hepatotoxic Effects of Tacrine Administration in Patients with Alzheimer's Disease," *JAMA* 271:992 (1994).

Whitehouse, P. J., "Cholinergic Therapy in Dementia," *Acta Neurol. Scand.* 149:42 (1993).

Tang, Xi-Can, "Huperzine A (Shuangyiping): A Promising Drug for Alzheimer's Disease," Acta Pharmacol. Sinica. 17:481-484 (1996).*

* cited by examiner

Huperzine-A

AChE activity and ACh Levels

COMPOSITIONS AND METHODS FOR TREATING OR PREVENTING NEURODEGENERATION AND COGNITIVE DECLINE AND DYSFUNCTION ASSOCIATED WITH ALZHEIMER'S DISEASE, AGING, OTHER DEMENTIA RELATED DISORDERS AND ESTROGEN DEFICIENCY RELATED CONDITIONS

CROSS-REFERENCES TO RELATED APPLICATIONS

This application claims the benefit of U.S. Provisional Application No. 60/141,189 filed Jun. 25, 1999.

BACKGROUND OF THE INVENTION

The present invention relates to compositions and methods for supplementing or complementing natural central nervous system hormonal and neurotransmitter activity to optimize global brain function, particularly in disorders associated with memory impairment. More specifically, the present invention relates to a composition comprising phytoestrogens and an acetylcholinesterase inhibitor for use in treating, retarding, or preventing neurodegeneration and cognitive decline and dysfunction associated with Alzheimer's disease (AD), aging, other related dementia disorders, and menopause.

The physiologic impact of estrogen deprivation, preceding and following the menopause, has a significant effect on the brain function and, hence, the quality of life for numerous women. A side variety of disorders may occur including, but not limited to, vasomotor instability with resulting hot flashes, disturbances in mood and affect, depression and irritability, spatial disorientation, and difficulty with verbal memory recall. Estrogen deprivation may also be an initiator or promotor of a series of biochemical abnormalities associated with the pathogenesis of Alzheimer's disease, senile dementia, and related conditions, including central nervous system (CNS) arteriosclerotic disease (also known as stroke). Impairment of balance involving cerebellar dysfunction and other postural mechanisms predisposes older postmenopausal women to falls, resulting in hip fractures and its consequences.

An individual's response to the menopausal transition depends on a number of variables, for example, genetic background, life-style factors (i.e., substance abuse, smoking), physical activity, response to chronologic aging, as well as the individual's brain "set-point" for estrogen. This, in turn, could depend on the distribution of beta and: alpha receptors in the brain and their affinity for either endogenous or exogenous estrogen.

A further manageable determinant of CNS dysfunction is the availability and reserve of the various CNS neurotransmitters. Senile dementia, especially Alzheimer's disease is a major disease associated with aging. Although the exact mechanisms responsible for senile dementia and Alzheimer's disease have not been elucidated, a growing body of evidence suggests that cholinergic neurons are essential for learning and memory processes [Bartus et al., Science 217:408 (1982); and Singh et al., Brain Research 644: 305 (1994)]. Alzheimer's disease is strongly associated with decreased choline acetyltransferase (ChAT) activity and (loss of cholinergic neurons [New England Journal of medicine 313:7 (Jul. 4, 1985); and Kosik, Science 256:780 (1992)]. The number of patients suffering with Alzheimer's disease and the costs associated with this disease are increasing dramatically with the increasing population of the elderly. About four million Americans (10% of the elderly at the age of 65 and 47% of the elderly at the age of 85 or higher) suffer with Alzheimer's disease [Evans et al., JAMA 262:2251 (1989)]. The incidence of dementia and Alzheimer's disease is reported to double every 5 years after the age of 65 [Jorm et al., Acta Psychiatr. Scand. 76:465 (1987)].

Currently, there is no cure for this devastating disease. Tremendous efforts have been undertaken to develop treatments for this disease. Treatment approaches which have been tested extensively include precursors for acetylcholine synthesis, cholinergic agonists, release enhancers and acetylcholinesterase (AChE) inhibitors. Various treatment approaches are shown below in Table 1.

TABLE 1

Cholinergic Treatment Strategies for Cognitive Decline in Alzheimer's Disease[1]

| Type | Effects on Cognitive Function |
| --- | --- |
| Precursors | |
| Choline | Unchanged/Slight Improvement |
| Lecithin | Unchanged/Slight Improvement |
| Cholinergic Agonists | |
| Pilocarpine | Unchanged |
| Arecoline | Unchanged/Slight Improvement |
| Oxotremorine | Unchanged |
| Bethanecol | Unchanged/Slight Improvement |
| Nicotine | Slight Improvement |
| CEE/Estradiol[2] | Improvement |
| Soy Phytoestrogens[3] | Improvement |
| Release Enhancers | |
| Phosphatidylserine | Slight Improvement |
| 4-aminopyridine | Unchanged/Slight Improvement |
| AChE Inhibitors | |
| Physostigmine | Unchanged to Significant Improvement |
| Tacrine | Unchanged to Significant Improvement |
| HupA[4] | Significant Improvement |

[1]From Messamore et al, Acta Neurol Scand 149:4 1993
[2]From Sherwin et al, Ann NY Acad Sci 743:213 1994
[3]From Pan et al, Proc Soc Exp Biol Med 221(2):118 1999; Neurosci Lett 261(1–2):17 1999
[4]From Skolnick, JAMA 278:1053 1997

Of these treatments, only AChE inhibitors like tacrine and physostigmine appear to be mildly effective in improving symptoms of Alzheimer's disease. For example, in some patients, these inhibitors increased the levels of acetylcholine in the brain. However, the major limitation of AChE inhibitor treatment is that cognitive function is improved only in patients whose brains still have a sufficient number of cholinergic neurons to synthesize acetylcholine. This treatment approach is totally ineffective in patients whose brains have suffered a serious loss of cholinergic neurons. Moreover, this treatment is not able to retard the loss of cholinergic neurons. In addition, tacrine has also been shown to be toxic to the liver [Watkins et al., JAMA 271:992 (1994)], and produces other undesirable side effects as well (see Table 2 below).

TABLE 2

Side Effects of Tacrine
(100 mg/day)

| Side Effect | Per Cent of Patients |
|---|---|
| Abdominal Cramps | 38 |
| Nausea | 25 |
| Polyuria | 25 |
| Diarrhea | 23 |
| Vomitin | 15 |
| Dizziness | 12 |
| Ptyalsim | 10 |
| Excessive Sweating | 4 |

From Beermann, Acta Neurologica Scandinavica 149:53 (1993)

The AChE inhibitor, physostigmine, has been found to exert mild beneficial effects on cognitive function in patients with Alzheimer's disease. Unfortunately, the short half-life of physostigmine renders this compound ineffective for use in treating Alzheimer's disease [Whitehouse, Acta Neurol. Scand. 149:42 (1993)].

STRUCTURE, SOURCE, AND ANTI-AChE PROPERTY OF HUPERZINE A

Recently, a novel AChE inhibitor, Huperzine A, has been reported to have selective and long-term inhibition of brain AChE with few side effects, and appears to be an effective treatment for improving cognitive function associated with cholinergic deficiency in patients with Alzheimer's disease [Tang, Acta Pharmacol. Sinica. 17:481(1996)].

Huperzine A (Hup A) was first isolated from Huperzia Serrata Trev and Chinese folk herb Qian Cheng Ta [Liu et al., Can J. Chem. 64:837 (1986)]. Hup A is a novel Lycopodium alkaloid [(5R, 9R, 11E)-5-amino-11-ethylidene-5,6,9,10-tetrahydro-7-methyl-5,9-methanocycloocta(b)pyridin2(1H)-one] as shown in FIG. 1. Hup A appears to be a much more potent and selective inhibitor of brain AChE than the other AChE inhibitors tested, and has few side effects [Tang, Acta Pharmacol. Sinica. 17:481 (1996)]. As shown below, Table 3 illustrates the in vivo anti-acetylcholinesterase activity of various AChE inhibitors in the blood and brain.

TABLE 3

Anti-acetylcholinesterase Activity (in vitro)
Blood (BuChE) vs Brain (AChE)

| | $IC_{50}$ (nmol/L$^{-1}$) | | Ratio of $IC_{50}$ |
|---|---|---|---|
| | BuChE | AChE | (BuChE/AChE) |
| Huperzine A | 58,894 | 58.4 | 1,008.5 |
| Tacrine | 74.6 | 93.0 | 0.8 |
| Physostigmine | 1259 | 251 | 5.0 |

In vivo animal studies indicated that Hup A can exert inhibition of brain AChE much longer than physostigmine (360 min vs 60 min) [Tang, supra, (1996)]. In fact, Hup A is very specific against AChE as indicated by the $IC_{50}$ values shown above in Table 3. In contrast, tacrine has a lower specificity for AChE, and also inhibits butyrylcholinesterase (BuChE) at an $IC_{50}$ value comparable to AChE. Studies further revealed that Hup A inhibits AChE in the cerebral cortex and, more importantly, in the hippocampus where acetylcholine synthesis was markedly reduced in Alzheimer's patients [Hallak and Giacobine, Neurochem. Res. 11:1037 (1986); and Tang, J., Neurosci. Res. 24:276 (1989)]. These results are illustrated in FIG. 2. In addition, Hup A appears to be effective in inhibiting AChE activity in the cerebral cortex, hippocampus, and other brain regions after chronic treatment in rats [Lagniere et al., Neuropharmacol. 30:763 (1991)]. These results are illustrated in FIG. 3.

The data collectively indicate that Hup A can be used to improve the symptoms of Alzheimer's disease in patients with fewer peripheral side effects as compared to other AChE inhibitors. The major limitation of Hup A, however, is that it cannot retard neurogeneration associated with Alzheimer's disease.

ESTROGEN PRESERVES THE INTEGRITY AND FUNCTION OF BRAIN CHOLINERGIC NEURONS

With respect to the use of hormone replacement therapy for treating Alzheimer's disease, estrogen has been shown to reduce the incidence of Alzheimer's disease and related dementias, relieve symptoms of Alzheimer's disease, preserve cholinergic function, and improve cognitive function in postmenopausal women and in patients with Alzheimer's disease [Sherwin, Ann. NY Acad. Sci. 743:213 (1994); and Paganini-Hill, Brit. J. Obstet. 103:80 (1996)]. This suggests that estrogen deficiency may be at least partially responsible for the neurodegeneration [Simpkins et al., Neurobiol. Aging 15: s195 (1994)]. This hypothesis is supported by the fact that estrogen deficiency results in decreased ChAT activity, and ChAT, BDNF, and NGF mRNAs, which can be reversed with an estrogen supplement [Luine, Exp. Neurol. 89:484 (1985); Gibbs et al., Exp. Neurol. 129:70 (1994); Singh et al., Abstr. Soc. Neurosci. 19:1254 (1993); Singh et al., Brain Res. 644:304 (1994); Singh et al., Endocrinol. 136:2320 (1995); and Sohrabji et al., Proc. Natl. Acad. Sci. USA 92:11110 (1995)].

Estrogen replacement in postmenopausal women appears to be the treatment of choice for reducing the incidence of dementia including Alzheimer's disease and improving the symptoms of Alzheimer's disease. However, traditional estrogen replacement therapy significantly increases the risk of breast and uterine cancers especially after long-term use, and also has intolerable side effects (e.g. menstrual bleeding, mood swings, and bloating) for some women [Levi et al., Eur. J. Cancer. 29A:1445 (1993); and Bergkvist and Persson, Drug Safety 15:360 (1996)]. These side effects may be nearly impossible to tolerate in women with dementia. Moreover, cancer risks have deterred widespread acceptance and use of estrogen replacement therapy as a treatment for various disorders associated with aging (including cognitive deficiency and dementia).

Soy phytoestrogens have also been studied to evaluate their effects on cognition. Soy phytoestrogens are plant analogs of estrogen, and have estrogen-like activity in some classical estrogen-responsive tissues. Since dietary intake of soy phytoestrogens is much higher in Japan and other Asian countries than in the U.S. and other Western countries, it has been speculated that soy phytoestrogens may account for the lower incidence of cardiovascular disease, breast cancer, and Alzheimer's disease in these Asian countries relative to the U.S. and other Western countries. Indeed, studies have demonstrated that soy phytoestrogens have no estrogenic effects on the breast and uterus [Foth and Cline, Am. J. Clin. Nutr. 68:14135(1998)], but retain the beneficial estrogenic effects on the cardiovascular system [Anthony et al., Arterio. Thrombo. Vasc. Biol., 17:2524 (1997)].

Co-inventors of the present invention have examined the effects of soy phytoestrogens on brain biomarkers, ChAT and brain-derived neurotrophic factor (BDNF). ChAT and BDNF are essential for normal cognitive function in retired breeder rats. Experimental results indicated that soy phytoestrogens up-regulate ChAT and BDNF mRNAs in the frontal cortex of retired breeder female rats just as estradiol does. Results suggest that soy phytoestrogens act as estrogen agonists in preserving the integrity and function of cholinergic neurons in the cerebral cortex, and may be used as an estradiol substitute in postmenopausal women to preserve cognitive function and in Alzheimer's patients to improve symptoms and retard further neurodegeneration [Pan et al., *Proc Soc Exp Biol Med* 221(2):118 (1999) and Pan et al., *Neurosci Lett* 261(1–2):17 (1999)].

STRUCTURE AND SOURCES OF PHYTOESTROGENS

Phytoestrogens are natural components of plants that mimic estrogen in animal tissues. For instance, some plants can induce estrus in animals largely due to the presence of phytoestrogens. To date, more than 300 plants have been identified that possess estrogenic activity. Phytoestrogens are classified into two chemical categories (coumestans and isoflavones), and have 15 carbon structures similar to the 17-carbon structure of estradiol shown below.

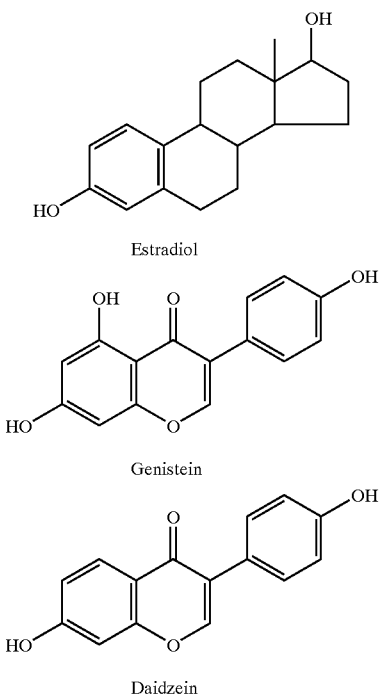

Legumes and grains are among food sources which have the highest content of isoflavones. For example, the content of isoflavones in soybeans ranges from approximately 0.5 to 3 mg per gram of soy protein. Dietary phytoestrogens appear to be readily absorbed in humans. Genistein, daidzein, and equol are the main isoflavones absorbed from the intestine, and are the metabolic products (of dietary isoflavones) generated by colonic bacteria which remove a glycoside moiety [King et al., *J. Nutr.* 126:176 (1997); and Sfakianos et al., *J. Nutr.* 127:1260 (1997)]. Dietary intake of soy phytoestrogens is much higher in Japan than in the U.S. and other Western countries. As a result, Japanese have a much higher blood concentration of phytoestrogens than adults in Western countries. Further, epidemiological studies show that the incidence of Alzheimer's disease in the elderly is lower in Japan than in the U.S. However, Japanese-Americans, who adopted a U.S. dietary style, were found to have developed Alzheimer's disease at a rate comparable to Americans [Graves et al., *Am. J. Epidemiol.* 144:760 (1996)]. These data suggest that high intake of dietary phytoestrogens may play an important role in reducing the incidence of Alzheimer's disease.

POSSIBLE MECHANISMS FOR THE BENEFICIAL EFFECTS OF SOY PHYTOESTROGENS ON BRAIN COGNITIVE FUNCTION

The mechanisms by which soy phytoestrogens, as well as estrogens, exert beneficial effects on brain cognitive function remain to be elucidated. Based on data collected by co-inventors of the present invention and indirect data concerning possible actions of soy phytoestrogens in mammalian cells by other researchers, the following mechanisms may account for the beneficial effects of soy phytoestrogens on brain cognition:

1. Soy phytoestrogens may act as estrogen agonists and exert protective effects on neurons including cholinergic neurons via estrogen receptors α and β (ER α and ER β). Isoflavones appear to be weak estrogens in vivo and in vitro. Genistein's affinity for ER α is about 20 times lower than that of estradiol. However, genistein's affinity for ER β is just 3 times lower than that of estradiol [Kuiper et al., *Endocrinol.* 138:863, (1997)]. Experimental data by co-inventors of the present invention demonstrates that both estradiol and soy phytoestrogens significantly up-regulate the levels of the mRNAs of ChAT, a reliable index of cholinergic function, and BDNF in the frontal cortex of retired breeder rats (see FIG. 4). [Pan et al., *Proc Soc Exp Biol Med* 221(2):118 (1999) and Pan et al., *Neurosci Lett* 261(1–2):17 (1999)]. Further, the co-inventors have further demonstrated that both ER α and ER β mRNAs are present in the frontal cortex and hippocampus of retired breeder rats. These data support the hypothesis that soy phytoestrogens as well as estradiol may directly interact with ER α and ER β to preserve cholinergic function in these regions [Pan et al., *Proc Soc Exp Biol Med* 221(2):118 (1999)].

2. Non-estrogen receptor-mediated mechanisms: Soy phytoestrogens may act as antioxidants [Ruiz-Larrea et al., *Free Radic Res* 26:63 (1997)] to protect neurons against oxidative damages and retard the neurodegeneration caused by oxidative damage. In addition, soy phytoestrogens may improve cerebral blood circulation and, therefore, improve oxygen and nutrient supply to cells in the brain.

EFFECT OF SOY PHYTOESTROGENS AND ESTRADIOL ON CHOLINE ACETYLTRANSFERASE AND BRAIN-DERIVED NEUROTROPHIC FACTOR mRNAS IN THE FRONTAL CORTEX OF RETIRED BREEDER RATS

A. Introduction

A growing body of evidence shows that postmenopausal estrogen replacement therapy (ERT) appears to be effective in reducing the risk of cardiovascular diseases, osteoporosis, and senile dementia (especially AD) [Clarkson et al., *Brit. J. Obstet. Gynaecol.* 103:53, (1996); Ettinger, *Obstet. Gynecol.* 72:12S, (1988); Knopp, *Obstet. Gynecol.* 72:23S, (1988); Paganini-Hill, *Brit. J. Obstet. Gynaecol.* 103:80 (1996); Speroff et al., *JAMA* 276:1397 (1996); Sullivan, *Brit. J.*

*Obstet. Gynaecol.* 103:59 (1996); and Tang et al., *Lancet* 348:429 (1996)]. The mechanisms by which estrogen preserves brain cognition are not known. Evidence suggests that estrogen may preserve brain cognition via a number of possible mechanisms including the maintenance of cholinergic function and interaction with neurotrophic factors, especially neurotrophic growth factor (NGF) and BDNF [Gibbs et al., *Exp. Neurol.* 129:70 (1994); Singh et al., *Abstr. Soc. Neurosci.* 19:1254 (1993); Singh et al., *Endocrinol.* 136:2320, (1995); and Sohrabji et al., *Proc. Natl. Acad. Sci. USA* 92:11110 (1995)]. Unfortunately, traditional estrogen replacement can significantly increase the risk of breast and uterine cancers, and has intolerable side effects for some women [Levi et al., *Eur. J. Cancer.* 29A: 1445 (1993); and Bergkvist and Persson, *Drug Safety* 15:360 (1996)].

It is conceivable that any compounds which can maintain normal levels of ChAT and BDNF in cholinergic neurons the basal forebrain (such as septum) and their target brain tissues (cerebral cortex and hippocampus) may reduce or even prevent loss of cholinergic neurons, and can be used in postmenopausal women to prevent Alzheimer's disease or to relieve the symptoms of Alzheimer's disease. It is of great importance to find compounds which retain the beneficial effects of estrogen on the brain cognitive function and Alzheimer's disease, but which do not have cancer-promoting effects in the breast and uterus, and other adverse effects. Soy phytoestrogens are among the promising candidates for this purpose, because they have no estrogenic effects on breast and uterus, but retain the beneficial estrogenic effects on cardiovascular system [Clarkson et al., *Trends Endocrinol. Metab.* 6: 11 (1995)]. To date, their effect on brain cognitive function and Alzheimer's disease has not been investigated.

The following study was designed to examine the effects of soy phytoestrogens and 17-β estradiol on ChAT and BDNF mRNAs in the frontal cortex and hippocampus of ovariectomized retired breeder rats.

B. Materials and Methods

Animals—15 rats (retired breeders weighing 300–360g) were purchased from Harlan Sprague Dawley, Inc. The rats were housed in separate cages, and were maintained on a 12:12 hour light/dark cycle with access to food and water ad libitum. All procedures performed on the animals were approved by the Animal Care and Use Committee at Wake Forest University School of Medicine.

Experimental procedure—Rats were randomized into three groups based on body weight. Three days after a bilateral ovariectomy, animals in groups 1, 2 and 3 were fed a control diet [Ctl diet, a casein/lactalbumin-based diet], a control diet supplemented with estradiol [E2 diet, 17β estradiol (Estrace™) purchased from Mead Johnson Laboratory] equivalent to a woman's dose of 2 mg/day, or a control diet supplemented with a soy phytoestrogen extract [SPE diet, soy phytoestrogens kindly provided by Protein Technologies International, St. Louis, Mo.] equivalent to a woman's dose of 150 mg total isoflavones/day, respectively. At the end of the eight-week treatment, the animals were euthanized with pentobarbital (100 mg/kg). Blood samples were collected by cardiac puncture at necropsy, and serum samples were used to determine estradiol and phytoestrogen levels. Brains were removed from the skull immediately after decapitation. Frontal cortex and hippocampus were dissected and frozen in liquid nitrogen. The frozen samples were then stored at −70° C. until RNA isolation.

RNA isolation—Total cellular RNA was isolated from tissues with TriZol Reagent (GIBCOL, BRL). The relative purity of isolated RNA was assessed spectrophotometrically, and the ratio of A260 nm to A280 nm exceeded 1.9 for all prep acetylcholinesterase inhibitor arations.

RT-PCR—RT-PCR was employed to detect the presence of BDNF and ChAT mRNAs in the brain samples, and to synthesize specific cDNA probes for Northern analysis of rat ChAT, BDNF and β-actin mRNAs. The primers used for ChAT, BDNF, and β-actin were selected in accordance with protocol from previous studies [Strauss et al., *Neurosci. Lett.* 168:193 (1994)]. The RT-PCR protocol was modified from the procedure reported by Pan et al., *Biochem. Biophy. Acta* 1307:233 (1996)] by optimizing the annealing temperature for these primer pairs (65° C.) and shortening the extension cycle time to 40 s. The modified PCR cycle conditions were 94° C. for 1 min, 65° C. for 1 min, and 72° C. for 40 s, followed by a final extension at 72° C. for 3 minutes. The specificity of the RT-PCR products was confirmed by sequencing analysis. The nucleotide sequences were 100% identical to those of published cDNA or mRNA sequences for ChAT, BDNF and β-actin.

Northern Analysis—RNA samples (30 ug) prepared from the frontal cortex or hippocampus were separated on 1.0% agarose gel by electrophoresis, then transferred to nylon membranes in 10×SSC at room temperature overnight (18 hours). The membranes were then subjected to a UV-cross linker and prehybridized at 42° C. for 4 hours. Finally, the membranes were incubated with ChAT, BDNF or β-actin-specific PCR probes at 42° C. for 20 hours. After incubation, the washed membranes were subjected to phosphoimager analysis. The optical density reading of ChAT or BDNF was normalized by the optical density reading of β-actin, which was obtained by reprobing the same membrane with β-actin-specific probe.

C. Results

Both BDNF and ChAT mRNAs were present in the frontal cortex and hippocampus regardless of treatment as indicated by the specific RT-PCR products. Both estrogen and phytoestrogens upregulated ChAT and BDNF mRNA levels in the frontal cortex of the retired breeder rats (see FIG. 4). ChAT and BDNF mRNA levels were comparable among OVX, E2, and soy phytoestrogen groups in the hippocampus of the retired rats.

D. Discussion

RT-PCR analysis indicates that ChAT mRNA is present in the frontal cortex and hippocampus of retired breeder rats, which confirms previous reports of the presence of ChAT mRNA in these two regions [Cavicchioli et al., *Brain Res. Mol. Brain Res.* 9:319 (1991); Lauterbom et al., *Brain Res. Mol. Brain Res.* 17:59 (1993)]. Northern analysis of total RNA isolated from the frontal cortex and hippocampus of both young and retired breeder rats revealed a 4.4 kb band, which is consistent with the reported size of ChAT mRNA in rats [Ishii et al., *Brain Res. Mol. Brain Res.* 7:151 (1990)]. Phosphoimager analysis of Northern blots indicates that ChAT mRNA levels were significantly higher in the frontal cortex of E2 and SBE groups as compared to the OVX controls, and were comparable in the hippocampus among treatments in the retired breeder rats. The data suggest that ChAT mRNA in different regions of the brain is not equally susceptible to estrogen deficiency. This theory is supported by previous experimental results which demonstrated that long-term ovariectomy reduced ChAT activity in the frontal cortex of rats by 50%, but had little impact on ChAT activity in the hippocampus [Singh et al., *Brain Res.* 644:305 (1994)]. The Singh et al. results suggest that the frontal cortex is more susceptible to estrogen deficiency than the hippocampus.

The co-inventors of the present invention have demonstrated that soy phytoestrogens are very effective in up-regulating ChAT mRNA in the frontal cortex of retired breeder rats under conditions of estrogen deficiency, suggesting that soy phytoestrogens may have a similar effect as estrogen in regulating ChAT mRNA. The data further indicated that both estradiol and soy phytoestrogens up-regulated BDNF mRNA levels in the frontal cortex of retired breeder rats, but had little impact on the BDNF mRNA levels in the hippocampus of retired breeder rats. This data is consistent with previous reports that BDNF mRNA in the cerebral cortex was regulated by estrogen status, and that estrogen replacement restored BDNF mRNA to normal levels in ovariectomized rats [Singh et al., *Endocrinol.* 136:2320 (1995)].

The mechanisms by which estrogen exerts its protective effect on brain cognitive function have yet to be determined. It is plausible that estrogen, as a member of the steroid hormone family, may function at least partially through its receptors [Brown, *Breast Cancer* 8:101 (1994)]. Two subtypes of estrogen receptors (ER α and ER β) have been reported [Green et al., *Nature* 320:134 (1986); Kuiper et al., *Proc. Natl. Acad. Sci. USA* 93:5925 (1996); and Mosselman et al., *FEBS* 392:49 (1996)]. ER β is reported to be the major subtype of ER in some regions of the brain [Kuiper et al., *Endocrinol.* 138: 863 (1997)]. Interestingly, genistein's binding affinity to ER β is only three times lower than the potent 17 β-estradiol [Kuiper et al., *Endocrinol.* 138:863 (1997)], which provides a molecular basis for soy phytoestrogens, or at least genistein, to interact with ER β and induce estrogenic effects. In addition, Sohrabji et al. [*Proc. Natl. Acad. Sci.* 92:11110 (1995)] demonstrated that the BDNF gene contained a putative estrogen response element. These data suggest that estrogen and soy phytoestrogens may directly regulate expression of the BDNF gene in the brain. Overall, the data indicate that soy phytoestrogens have similar effects as estrogen in preserving ChAT and BDNF mRNA levels in the frontal cortex of retired breeder rats.

Currently, there is no known cure for neurodegeneration and cognitive decline and dysfunction associated with Alzheimer's disease, aging, other related dementia disorders, and estrogen deficiency related conditions. Although different treatment approaches have been used as described herein, each has disadvantages which limit their effectiveness and/or produce serious side effects. Thus, there remains a need for a therapeutic which is effective in treating, retarding, and/or preventing neurodegeneration and cognitive decline and dysfunction associated with Alzheimer's disease and other related dementia disorders.

SUMMARY OF THE INVENTION

The present invention is directed to compositions and methods for treating, retarding, or preventing neurodegeneration and cognitive decline and dysfunction, particularly in disorders associated with memory impairment. The co-inventors of the present invention recognize the benefits of three compounds, phytoestrogens, mammalian estrogens, and acetylcholinesterase inhibitors, in combination to reduce or prevent loss of cholinergic neurons and to improve cognitive function and memory in mammals. The compositions of the present invention are suitable for use in treating those individuals with or at risk of developing Alzheimer's disease, aging associated cognitive disorder (i.e., age associated memory impairment), other dementia related disorders, benign senescent forgetfulness, mild cognitive disorder, and estrogen deficiency related conditions. Preferably, those individuals include normal cycling pre-perimenopausal women, menopausal women, post-menopausal women, and men with aging related cognitive disorders. As an additional benefit, the present compositions overcome the disadvantages associated with current estrogen replacement therapies. Further, the synergism between the three compounds allows for a more effective lower dose therapy with fewer side effects as compared to other known therapeutics.

Given the numerous processes and functions of brain-regulated activities, the present invention seeks to provide both a specific therapeutic (memory) and a more general approach to mental well-being. In this regard, a pharmaceutical composition for administration to mammals is disclosed, comprising a combination of at least one mammalian estrogen and at least one acetylcholinesterase inhibitor in an amount sufficient to enhance memory and concentration in mammals. Further, a composition for enhancing memory and concentration is disclosed, which comprises a combination of at least one phytoestrogen and at least one acetylcholinesterase inhibitor, or any derivative, analog, or metabolite of the phytoestrogen and the acetylcholinesterase inhibitor, or any combination thereof. The composition includes dietary supplements, nutraceuticals, and food additives. It is contemplated that the pharmaceutical composition and the dietary supplement can be used to improve cognitive function, particularly in disorders associated with memory impairment such as Alzheimer's disease, aging, other dementia related disorders, and estrogen deficiency related conditions.

In one aspect of the present invention, the composition comprises a combination of at least one phytoestrogen and at least one acetylcholinesterase inhibitor, or any derivative, analog, or metabolite of the phytoestrogen and the acetylcholinesterase inhibitor, or any combination thereof. The phytoestrogen is an isoflavone, coumestan, lignan, or any combination thereof. The phytoestrogenic isoflavone is selected from at least one of genistein, daidzein, biochanin A, formononetin, glycitein, the natural glycosides, or metabolites thereof. The phytoestrogen is derived from soy, clover, legumes, kudzu root, oilseeds, or any other phytoestrogen containing plant, or chemically synthesized. The acetylcholinesterase inhibitor is selected from at least one of the following: lycopodium alkaloids (i.e, Huperzine A and Huperzine B), piperidine-based inhibitors (i.e, Donepezil), carbamate-based inhibitors (i.e., Physostigmine, ENA-713 (Exelon or rivastigmine, a phenylcarbamate derivative), eptastigmine)), acridine-based inhibitors (Tacrine), alkaloids of the common snowdrop (i.e., Galanthamine), organophosphate cholinesterase inhibitors (i.e., Metrifonate, 2,2-dimethyldichlorovinyl phosphate (DDVP), hybrid of Huperzine A and Tacrine (i.e., Huperzine X) or any derivative, analog, metabolite or combination thereof. The composition includes about 0.5 mg to about 1000 mg phytoestrogen and about 0.01 mg to about 150 mg acetylcholinesterase inhibitor.

In another aspect, the present invention is a composition comprising a combination of at least one mammalian estrogen and at least one acetylcholinesterase inhibitor, or any derivative, analog, or metabolite of the mammalian estrogen and the acetylcholinesterase inhibitor, or any combination thereof. The mammalian estrogen is selected from the group consisting of estradiol, conjugated equine estrogens (CEE), any active estrogenic ingredients of CEE, estrone, estriol, esterified estrogens, and any derivative, analog, or metabolite of the mammalian estrogen. The estradiol is 17-β estradiol, estradiol valerate, ethinyl estradiol, or any other estradiol derivative, analog, or metabolite thereof. The composition includes about 0.2 mg to about 2 mg mammalian estrogen and about 0.01 mg to about 150 mg acetylcholinesterase inhibitor.

In another aspect of the invention, the composition comprises a combination of at least one phytoestrogen, at least one mammalian estrogen, and at least one acetylcholinesterase inhibitor, or any derivative, analog, or metabolite of the phytoestrogen, mammalian estrogen and the acetylcholinesterase inhibitor, or any combination thereof. The composition includes about 0.01 mg to about 1000 mg phytoestrogen, about 0.2 mg to about 2 mg mammalian estrogen, and about 0.01 mg to about 150 mg acetylcholinesterase inhibitor.

In another aspect of the present invention, a method is disclosed for treating, retarding or preventing memory impairment in mammals, comprising co-administering a combination of at least one phytoestrogen and at least one acetylcholinesterase inhibitor, or any derivative, analog or metabolite of the phytoestrogen and the acetylcholinesterase inhibitor, or any combination thereof in a therapeutically effective amount. The combination may further include at least one mammalian estrogen in a therapeutically effective amount for co-administration. Alternatively for administration, the combination can include at least one mammalian estrogen and at least one acetylcholinesterase inhibitor.

Any of compositions of the present invention may be prepared in a dosage form selected from the group consisting of a pill, capsule, tablet, powder, beverage, suspension, emulsion, syrup, solution, patch, gel, and the like. For administration purposes, the compositions may further include pharmaceutically acceptable carriers, diluents, stablizers, solubilizers, lubricants, binders and the like or excipients thereof The term "estrogen deficiency related condition" is used to refer to conditions associated with menopause, the surgical removal of the ovaries, and ovary dysfunction.

The term "therapeutically effective amount" as used herein is defined as the dose which provides effective treatment or prevention for mammals, in particular humans, for the conditions, disorders, and diseases described herein.

The proceeding and further objects of the present invention will be appreciated by those of ordinary skill in the art from a reading of the detailed description of the preferred embodiments which follow, such description being merely illustrative of the present invention.

DESCRIPTION OF THE PREFERRED EMBODIMENTS

Phytoestrogens and mammalian estrogens are able to retard neurodegeneration in post-menopausal women and individuals with Alzheimer's disease. The symptoms of Alzheimer's disease are improved by preserving cholinergic neurons and increasing ChAT activity, acetylcholine synthesis and neurotrophic factors. On the other hand, acetylcholinesterase inhibitors, in particular Hup A, are able to improve cognitive function in post-menopausal women and individuals with Alzheimer's disease by increasing acetylcholine levels in the brain through the inhibition of AChE activity. The co-inventors of the present invention recognize the benefits of all three compounds for use in the treatment or prevention of disorders associated with memory impairment. These disorders include, but are not limited to, Alzheimer's disease, aging, other dementia related disorders and estrogen deficiency related conditions.

The present compositions comprise different combinations of the phytoestrogens, mammalian estrogens, and the acetylcholinesterase inhibitors or any of their derivatives, analogs, metabolites or any combinations thereof. In a preferred aspect of the invention, the composition comprises at least one phytoestrogen and at least one acetylcholinesterase inhibitor, preferably Hup A. Such a composition is suitable for use as a dietary supplement for enhancing memory and concentration in humans. It is contemplated that the composition would be used by individuals desiring to enhance their memory, reduce or prevent neurodegeneration and cognitive decline, delay the onset of Alzheimer's disease and related dementias, relieve the symptoms of Alzheimer's and related dementias, or to treat estrogen deficiency related conditions.

In another aspect of the invention, the composition comprises a combination of at least one phytoestrogen, at least one mammalian estrogen, and at least one acetylcholinesterase inhibitor, preferably Hup A. With the combination of the mammalian estrogen and the acetylcholinesterase inhibitor, a composition is produced that is suitable for use as a pharmaceutical for enhancing memory and concentration in individuals with or at risk of developing neurodegeneration and cognitive decline, Alzheimer's disease aging, other dementia related disorders or an estrogen deficiency related condition.

Any mammalian estrogen and effective acetylcholinesterase inhibitor may be used in the compositions and the methods in accordance with the present invention. Preferably, the estrogen is estradiol and the acetylcholinesterase inhibitor is Hup A or any derivative, analog or metabolite of either compound.

Figure 1:
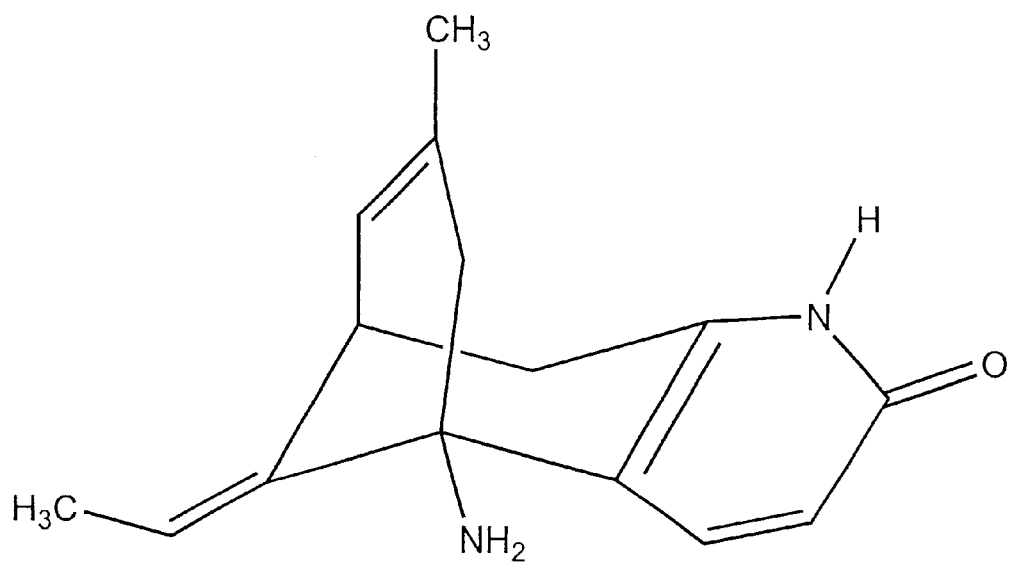
FIG. 1 illustrates the chemical structure of Huperzine A [(5R, 9R, 11E)-5-amino-11-ethylidene-5,6,9,10-tetrahydro-7-methyl-5,9-methanocycloocta(b)pyridin2(1H)-one]
Figure 2:
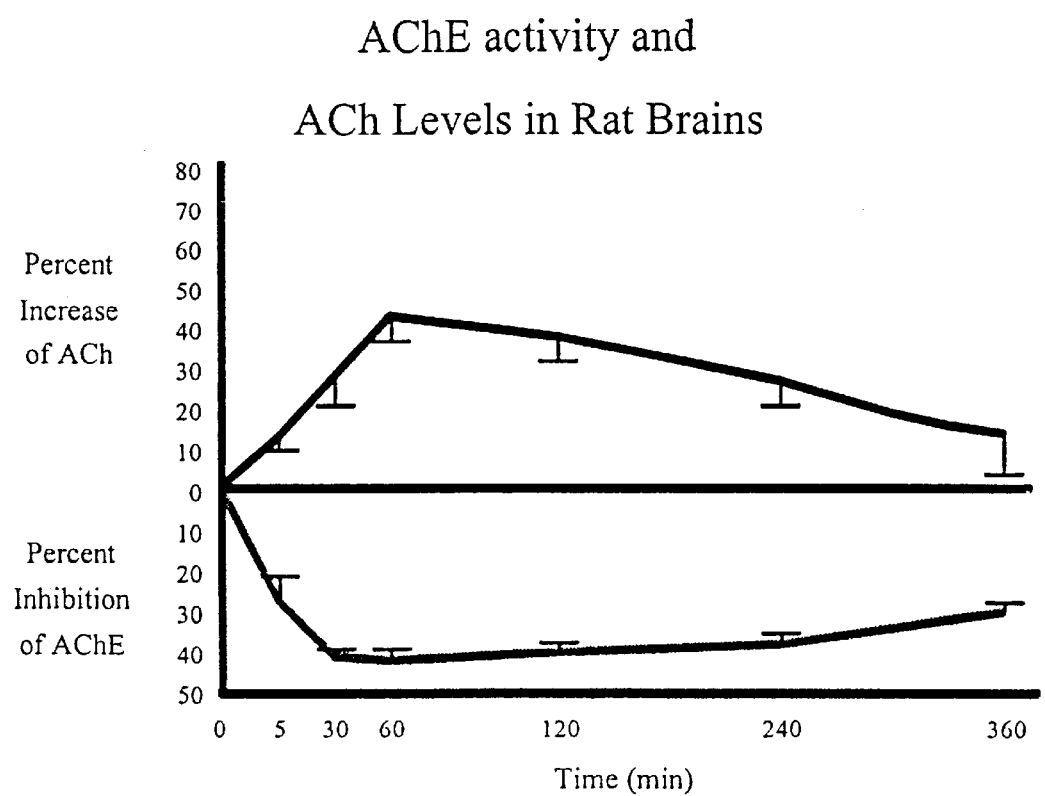
FIG. 2 illustrates the inhibitory effects of Huperzine A on AChE in the cerebral cortex.
Figure 3:
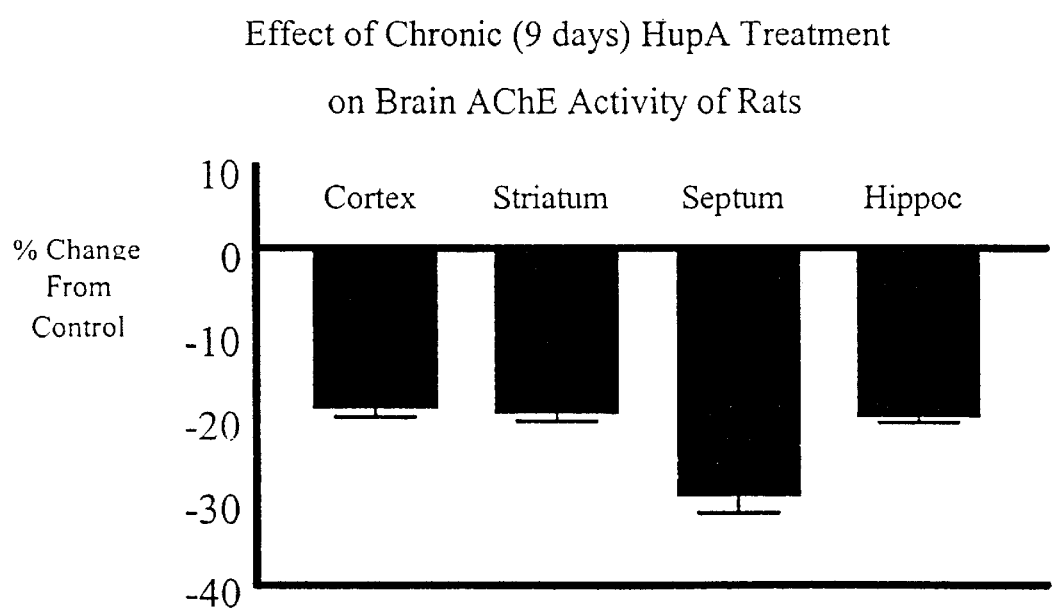
FIG. 3 illustrates the effect of chronic (9 days) Huperzine A treatment on brain AChE activity in rats.
Figures 4A, 4B:
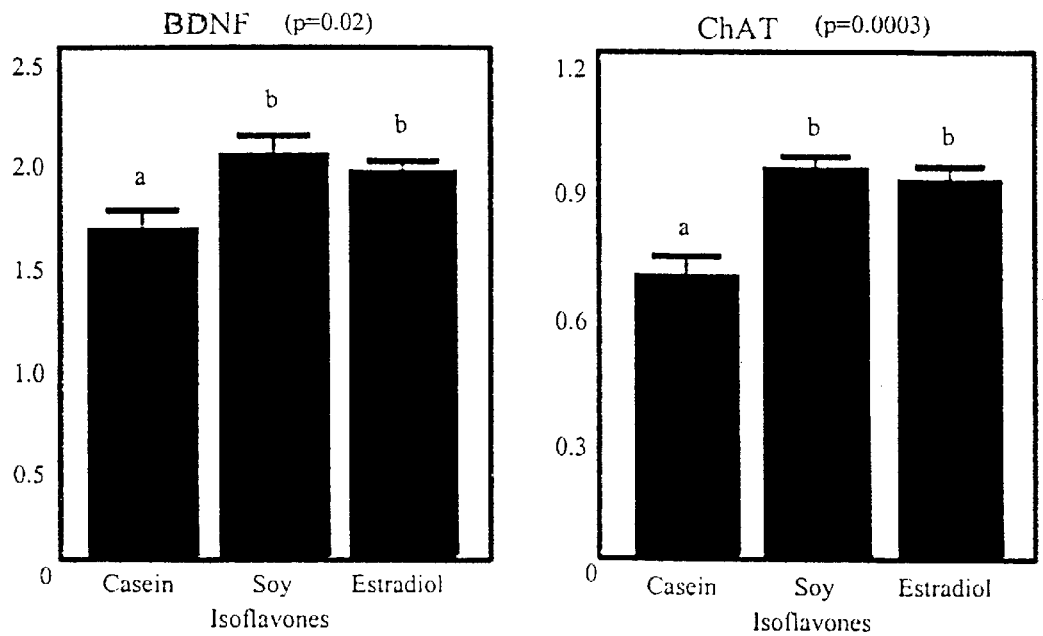
FIG. 4 illustrates the effects of estradiol and soy isoflavones on brain-derived neurotrophic factor and choline acetyltransferase mRNA.
Figure 5:
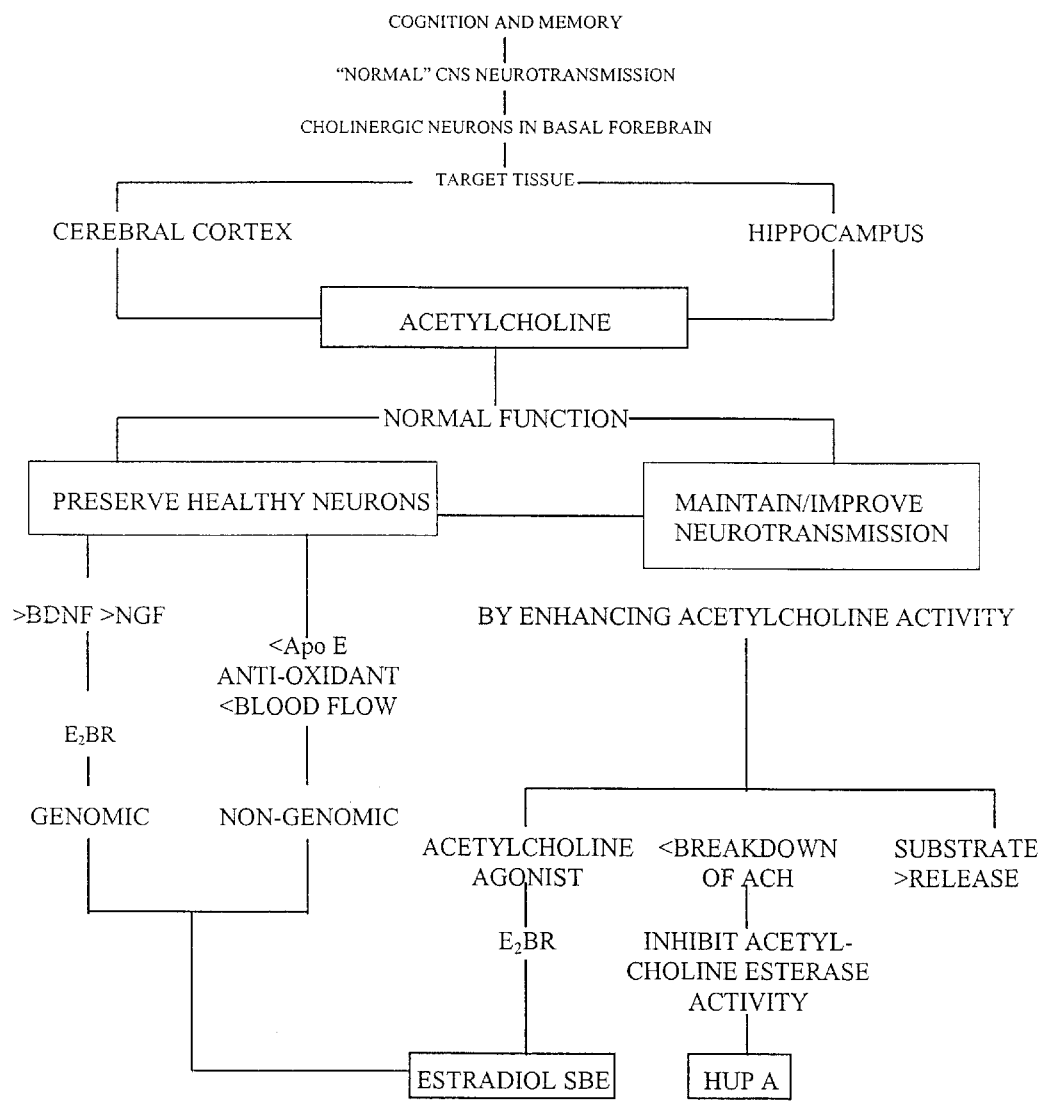
FIG. 5 is a schematic diagram of the mechanisms of action for the compositions of the present invention.

FIG. 5 is a schematic diagram of the mechanisms of action for the compositions of the present invention. By its genomic CNS interaction with estrogen receptors in the brain (hypothalamus; cerebral cortex; limbic system and hippocampus) and additional on-genomic activity, the following estrogen-influenced positive CNS events can be emonstrated:

A. upgrade in the synthesis and activity of ChAT, BDNGF and other associated factors;

B. stimulation of dendritic growth;

C. estrogen reduces the deposition of β-amyloid;

D. improvements in cerebral and cerebellar blood flow and vasodilatory response to acetylcholine in women with cerebrovascular disease;

E. improvement in serotonin biochemistry, synthesis and release; and

F. a CNS anti-oxidant.

With respect to phytoestrogens, their actions are independent of mammalian estrogen on ChAT, BDNF, NGF, and other related compounds. By a demonstrated synergistic action with estrogen, the dose of estrogen otherwise needed for appropriate CNS activity may be reduced. This will decrease potential estrogen-induced side effects and concerns. Due to soy phytoestrogen demonstrated estrogen-antagonism in breast and endometrial tissue, naturally menopausal women (the majority of women experiencing menopause) can be treated without the addition of progestins normally required for endometrial protection. Progestins down-regulate estradiol receptors, and could also antagonize the vasodilatory capability of estrogen in women with cerebrovascular disease.

Because of its unique efficacy and safety as an acetylcholinesterase inhibitor, Hup A should improve the availability of acetylcholine, thus, enhancing and improving memory, and probably other as yet undetermined CNS functions.

The estrogen component of the compositions of the present invention is selected from all commercially available estrogens (mammalian, plant and the like) and at all dosages. The estrogen may include estradiol, conjugated equine estrogens (CEE), any active estrogenic ingredients of CEE, estrone, estriol, esterified estrogens, or any derivative, analog or metabolite of the estrogen. The estradiol is 17-β estradiol, estradiol valerate, ethinyl estradiol, or any other estradiol derivative, analog, or metabolite. Similarly, the phytoestrogen component of the composition will include all commercially available phytoestrogens and at all dosages. All routes of administration for the compositions may be used, which include the following: pill, capsule, tablet, powder, beverage, suspension, emulsion, syrup, solution, patch, gel, and the like. For administration purposes, the compositions may further include pharmaceutically acceptable carriers, diluents, stablizers, solubilizers, lubricants, binders and the like or excipients thereof. It is further contemplated that the following dosage combinations may include, but are not limited to, high, low, intermediate, continuous, and intermittent for all combinations of the estrogen, acetylcholinesterase inhibitor, and phytoestrogen.

The classes of phytoestrogens that may be used in the present invention include isoflavones, coumestans, lignans or any combination thereof. The isoflavones which display estrogenic activity are preferred and include genistein, daidzein, biochanin A, formononetin, glycitein, the natural glycosides or metabolites of any of the isoflavones. The preferred phytoestrogens are extracted from soy; however, other sources may be used including clover, legumes, kudzu root, oilseeds, or any other phytoestrogen containing plants, or chemically synthesized phytoestrogens.

The acetylcholinesterase inhibitor component of the compositions is selected from at least one of the following: lycopodium alkaloids (i.e, Huperzine A and Huperzine B), piperidine-based inhibitors (i.e, Donepezil), carbamate-based inhibitors (i.e., Physostigmine, ENA-713 (Exelon or rivastigmine, a phenylcarbamate derivative), eptastigmine)), acridine-based inhibitors (Tacrine), alkaloids of the common snowdrop (i.e., Galanthamine), organophosphate cholinesterase inhibitors (i.e., Metrifonate, 2,2-dimethyldichlorovinyl phosphate (DDVP), hybrid of Huperzine A and Tacrine (i.e., Huperzine X) or any derivative, analog, metabolite or combination thereof. The composition includes about 0.01 mg to about 1000 mg phytoestrogen and about 0.01 mg to about 150 mg acetylcholinesterase inhibitor.

A method for improving memory and concentration in mammals is disclosed. The method comprises the step of co-administering the combination of at least one phytoestrogen and at least one acetylcholinesterase inhibitor, or any derivative, analog, or metabolite of the phytoestrogen and the acetylcholinesterase inhibitor, or any combination thereof in a therapeutically effective amount. The combination is administered to mammals, preferably humans, who are suffering with or at risk of developing memory impairment associated with Alzheimer's disease, aging, other dementia related disorders, and estrogen deficiency related conditions. The estrogen deficiency related conditions that are targeted for treatment purposes include, but are not limited to, menopause, the surgical removal of the ovaries, and ovary dysfunction.

Each component of the compositions, the phytoestrogen, the mammalian estrogen, and the acetylcholinesterase inhibitor can be co-administered concurrently, sequentially, or randomly. Preferably, the components are co-administered concurrently in a composition of the present invention described hereinabove on a regular basis. When co-administered sequentially, the phytoestrogen, the mammalian estrogen, and the acetylcholinesterase inhibitor are administered as separate components on a regular basis, where each component is adminstered according to the selected dosage prior to another administration of the other component(s). When co-administered randomly, the phytoestrogen, the mammalian estrogen, and the acetylcholinesterase inhibitor are administered in no particular order on a regular basis in amounts effective to maintain the desired combined therapeutic effect of the pre-selected combination.

EXAMPLE 1

EFFECT OF SOY PHYTOESTROGENS AND ESTRADIOL ON WORKING MEMORY IN ESTROGEN-DEFICIENENT RATS

A. Objective

The main objective was to examine the effects of oral estradiol alone, soy protein with phytoestrogens alone, and combinations of estradiol and soy phytoestrogens on working memory of ovariectomized retired breeder female rats using the radial arm maze test (Pan, Y, Anthony M S, Watson S, Clarkson T B. Soy Phytoestrogens Improve Radial Arm Maze Performance in Ovariectomized Retired Breeder Rats and do not Attenuate Benefits of 17-β Estradiol Treatment. Menopause, in press).

B. Materials and Methods

Animals

Eight-four retired breeder females (Sprague-Dawley), weighing 300–360 g (8–10 months old), were purchased from Harlan Sprague Dawley, Inc. The rats were housed in separate cages and were initially maintained on a 12:12 hour light/dark cycle with access to Chow diet and water ad libitum. All procedures done on the animals were approved by the Animal Care and Use Committee of Wake Forest University. Upon arrival, the rats were weighed, and then randomized into the 12 treatment groups using a stratified randomization scheme, stratifying by body weight.

The ingredients and composition of the control diet and the two soy phytoestrogen diets are presented in Table 4.

TABLE 4

Diet Composition[a]

| INGREDIENT | Control Diet g/100 grams | Middle SPE Diet g/100 grams | High SPE Diet g/100 grams |
|---|---|---|---|
| Casein | 10.50 | 5.25 | — |
| Lactalbumin | 10.00 | 5.00 | — |
| SUPRO 670 HG[b] | — | 10.13 | 20.25 |
| DL-methionine | — | 0.25 | 0.5 |
| Dextrin | 30.80 | 30.80 | 30.80 |
| Sucrose | 28.00 | 28.00 | 28.00 |
| Alphacel | 10.00 | 10.09 | 10.18 |
| Lard | 5.20 | 5.20 | 5.20 |
| Safflower Oil | 1.00 | 0.78 | 0.57 |
| AIN-76A Vitamin Mix | 1.00 | 1.00 | 1.00 |
| AIN-76 Mineral Mix | 3.50 | 3.50 | 3.50 |

[a]Estrace containing 1 mg 17-β estradiol per tablet was added to either the control diet or the SPE diets to achieve the doses of 0.5 mg/1800 Cal (0.1 tablet per 100 grams diet), 1.0 mg/1800 Cal (0.205 tablet per 100 grams diet), and 2.0 mg/1800 Cal (0.41 tablet per 100 grams diet). SPE-$E_2$ combination diets consist of either middle dose or high dose SPE diets with corresponding doses of $E_2$ added.
[b]SUPRO 670-HG is a phytoestrogen intact soy protein isolate provided by Protein Technologies International and contains 1.69 mg phytoestrogens (genistein and daidzein) per gram protein isolate.

Shown in Table 5 below is the 3×4 factorial study design and includes the number of rats that finished the maze tests. The treatment diets were started three days after a bilateral ovariectomy and animals were fed 40 g/day of the assigned diet for 10 months. Five rats died during the treatment phase.

TABLE 5

Treatment Diets and Number of Rats Tested Per Treatment

| | 17-β estradoil (Estrace ™) mg/1800 Cal (mg/kg BW) | | | |
|---|---|---|---|---|
| SPE/1800 Cal. (mg/kg BW) | 0 (0) | 0.5 (0.018) | 1 (0.036) | 2 (0.071) |
| 0 mg (0 mg) | N = 5 | N = 6 | N = 7 | N = 7 |
| 72 mg (8.5 mg/kg) | N = 5 | N = 5 | N = 6 | N = 6 |
| 144 mg (17 mg/kg) | N = 5 | N = 7 | N = 6 | N = 6 |

*SPE = soy phytoestrogens;
BW = body weight.

Material

Oral micronized estradiol ($E_2$) (17-β estradiol—Estrace™) was purchased from Mead Johnson Laboratory and the soy protein isolate with phytoestrogens (SPE) was provided by Protein Technologies International, St. Louis, Mo.

Radial Arm Maze Setup

An eight-arm radial maze was used since it has been shown to be sensitive to estrogen status in previous studies. The maze had a central platform with eight arms (62 cm long by 12 cm wide by 18 cm high) with transparent sides and tops. Each arm had a food well at the end of the arm. The maze was mounted on a table in a white-painted room with a dim light. Visual cues were placed between the arms, at the entrance of the arm, and on the walls near the maze.

Radial Arm Maze Training

A pellet of fudge brownie (Little Debbie, Mckee Foods, Collegedale, Tenn.) was placed in each of the 8 food wells located at the end of each arm to serve as a reward. The rats were allowed to explore the maze for 10 min or until all eight rewards were eaten. The training session was terminated when the rats were able to eat all 8 rewards within 10 min.

Radial Arm Maze Test

After the training, the rats were tested twice per day (in the morning and afternoon) 4 consecutive days per week for two weeks. One day prior to the test, and during the first three test days, the food intake was reduced to 25% of the normal 40 g/day food intake. A visit to an arm was recorded if the rat reached three-fourths of the length of the arm. The maze performance was recorded as the number of correct choices in the first 8 visits. A mistake was counted if a rat reentered an arm from which the rat has already eaten the bait. A test session of a rat was terminated when the rat ate all eight rewards or 10 min had elapsed. If a rat has a perfect working memory, the rat should score 8 correct choices in the first 8 visits (or eat all eight baits without re-visiting an arm from which the rat has already eaten the bait). The number of correct choices in the first 8 visits equals 8 minus the number of mistakes in the first 8 visits. After the test, the mean of the 16 test results of a given rat was used in the statistical analyses. The rats in the 0 mg (group without $E_2$ or SPE supplementation), 2 mg $E_2$ and 144 mg SPE groups were tested after three months, 6 months and 10 months of treatment, but only the 10 month data are included in this report. The rats in other groups were tested after 10 months of treatment. Five rats died during the treatment phase. Eight rats were disqualified from the test for refusing to move in the maze. There were no treatment effects on the number of rats that were disqualified from the test. 71 out of the 84 rats were tested and their data were used in the analyses.

Uterus and Body Weight

The body weights of the rats were recorded every two weeks during the study and at necropsy. At the end of the study, the rats were euthanized with pentobarbital (100 mg/kg). The uteri were collected and their weights were determined with an electronic balance.

Statistical Analyses

All data were analyzed using BMDP Statistical Software, version 7.0 (Los Angeles, Calif.). Uterine weights expressed as a percentage of body weight and body weight violated the assumption of equal variances, and were not normally distributed. Therefore a square root transformation of these data was calculated and the analyses were done on the transformed data. The means and standard errors have been re-transformed into the original units. All other data shown are means±standard error of the mean (SEM). Body weight, uterine weight, and maze data were analyzed by 2-way ANOVA. Dose-response relationships for $E_2$-only or SPE-only treatments were tested using multiple regression. Between-group comparisons were analyzed by the Student-Newman-Keuls multiple range test which adjusts for multiple comparisons. P-values for the tests for antagonism by SPE within each dose of $E_2$ on radial arm maze performance are Bonferroni adjusted p-values accounting for 2 comparisons within each dose of $E_2$. P-values<0.05 were considered to be statistically significant.

C. Results

Figures 7A, 7B:
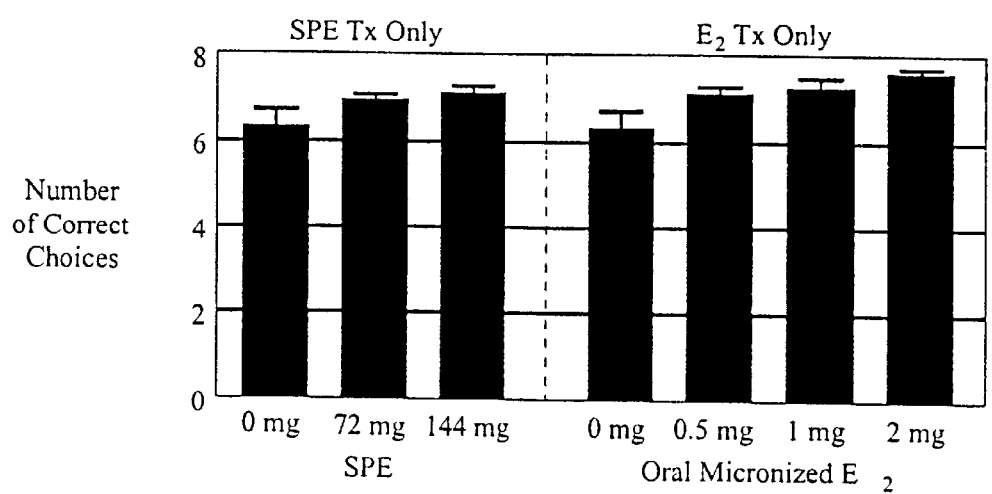
FIG. 7 illustrates the effects of oral administration of estradiol, or soy with phytoestrogens in rats in the performance of the radial arm maze tests.

Oral administration of estradiol, or soy with phytoestrogens, resulted in a dosedependent improvement in the performance of the radial arm maze tests (see FIG. 7). In addition, at each of the three doses of oral micronized estradiol tested, the performance of the radial arm tests were not significantly different in the presence or absence of soy with phytoestrogens. These data suggest that soy phytoestrogens may function as estrogen agonists in improving working memory in the ovariectomized retired breeder female rats and that soy phytoestrogens do not antagonize the beneficial effects of estradiol on the working memory of these rats.

EXAMPLE 2

EFFECTS OF SOY PHYTOESTROGENS AND ESTRADIOL ON WORKING MEMORY DEFICIENCY IN CHRONIC ESTROGEN-DEFICIENT RATS

A. Objectives

The second study was designed to investigate whether soy phytoestrogens or estradiol can reverse working memory deficiency in aged ovariectomized rats and, further, whether the addition of Hup A to the soy or estradiol treatments would result in further benefit in improving working memory.

B. Materials and Methods

Animals

Thirty-six retired breeder female rats (8–10 months old) were purchased from Harlan Sprague Dawley, Inc. The rats were housed in separate cages and were initially maintained on a 12:12 hour light/dark cycle with access to Chow diet and water ad libitum. All procedures done on the animals were approved by the Animal Care and Use Committee of Wake Forest University. After bilateral ovariectomy, the rats were fed with a casein/lactalbumin-based control diet for about 12 months (until about 2 years of age). The rats were then evaluated in a 8-arm radial arm maze to determine their baseline working memory. The rats were then randomized into one of 3 groups and fed with the control diet (Ctl), or the control diet supplemented with 2 mg/1800 Cal 17-62 estradiol (E2), or a soy protein-based diet containing 144 mg/1800 Cal soy phytoestrogens (SPE). The rats were tested in the maze at 1 and 3 months after the initiation of the treatments.

After 3 months of treatment, each of the 3 groups were divided randomly into two subgroups. One subgroup was given Hup A orally (0.3 mg/Kg of body weight) in addition to their control regimen or treatment with SPEs or $E_2$ and the other subgroup received no Hup A. After 3 weeks of Hup A supplementation, working memory was reevaluated.

Material

Oral micronized estradiol ($E_2$) (17-beta-estradiol—Estrace™) was purchased from Mead Johnson Laboratory and the soy protein isolate with phytoestrogens (SPE) was provided by Protein Technologies International, St. Louis, Mo. Huperzine A was purchased from Marcro Hi-Tech, JV Ltd.

Radial Arm Maze Training

A pellet of fudge brownie (Little Debbie, Mckee Foods, Collegedale, Tenn.) was placed in each of the 8 food wells located at the end of each arm to serve as a reward. The rats were allowed to explore the maze for 10 min or until all eight rewards were eaten. The training session was terminated when the rats were able to eat all 8 rewards within 10 min.

Radial Arm Maze Test

After the training, the rats were tested once per day 4 consecutive days per week for two weeks. One day prior to the test, and during the first three test days, the food intake was reduced to 25% of the normal 40 g/day food intake. A visit to an arm was recorded if the rat reached three-fourths of the length of the arm. The maze performance was recorded as the number of correct choices in the first 8 visits. A mistake was counted if a rat reentered an arm from which the rat has already eaten the bait. A test session of a rat was terminated when the rat ate all eight rewards or 10 min had elapsed. If a rat has a perfect working memory, the rat should score 8 correct choices in the first 8 visits (or eat all eight baits without re-visiting an arm from which the rat has already eaten the bait). The number of correct choices in the first 8 visits equals 8 minus the number of mistakes in the first 8 visits. After the test, the mean of the 8 test results of a given rat was used in the statistical analyses.

Uterus and Body Weight

The body weights of the rats were recorded every two weeks during the study and at necropsy. At the end of the study, the rats were euthanized with pentobarbital (100 mg/kg). The uteri were collected and their weights were determined with an electronic balance.

Statistical Analyses

All data were analyzed using BMDP Statistical Software, version 7.0 (Los Angeles, Calif.).

C. Results

After 12 months of estrogen-deficiency, the rats had very poor maze performance. The maze performance (working memory) of the rats in $E_2$ and SPE groups was significantly better than that of the Ctl group at both 1 and 3 months of treatments (P=10 0.0001).

Figure 6A:
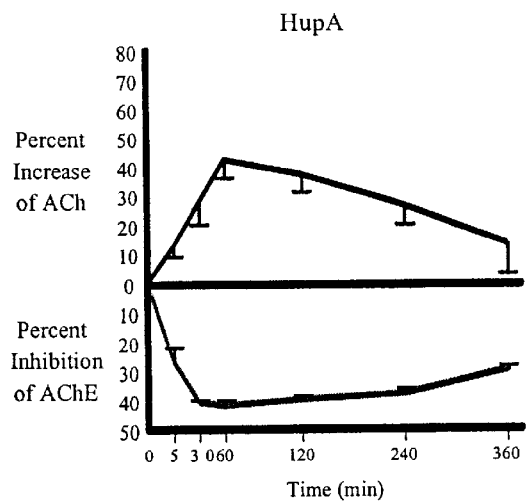
FIG. 6 illustrates the acetylcholine (ACh) levels following the administration of Huperzine A (see Tang) verus the combination of soy phytoestrogens and Huperzine A or estrogen and Huperzine A.
Figure 6B:
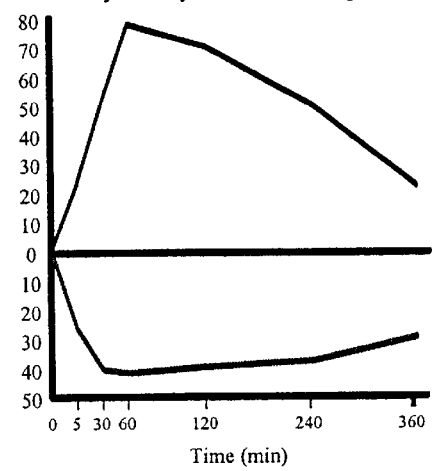
Figure 8:
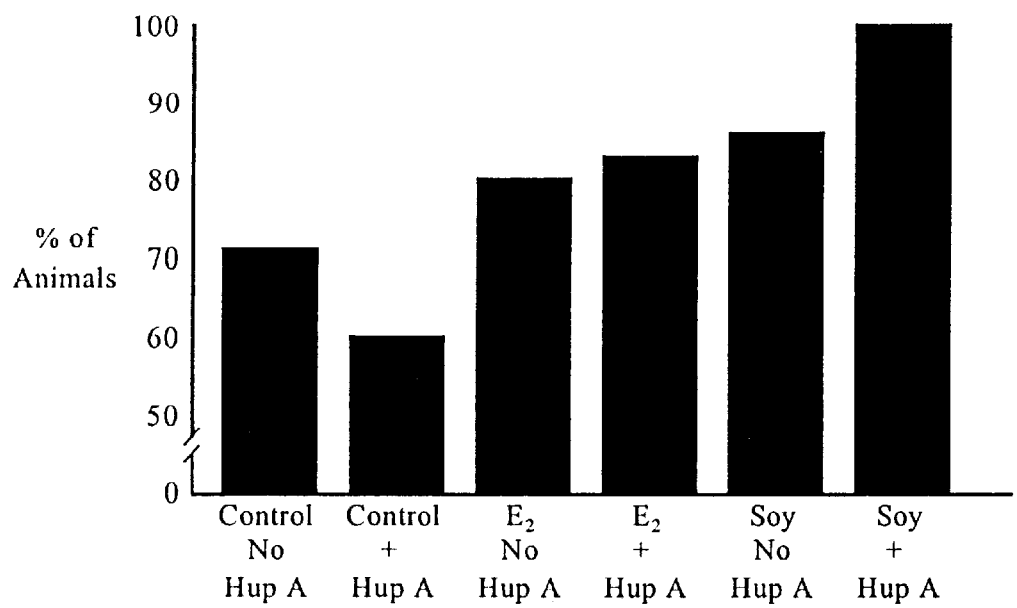
FIG. 8 illustrates the effect of Huperzine A treatment on proportion of animals with cognitive improvement following $E_2$ or soy phytoestrogen treatment.

The results concerning the effects of the combinations of soy phytoestrogen or estradiol with Hup A on working memory deficiency are summarized in FIG. 8. The results are expressed as the proportion of the animals that had improved working memory after receiving Hup A or no Hup A. Cognitive function was considerably improved when Hup A was added to SPE treatment and slightly improved when Hup A was added to $E_2$ treatment. It is expected that the combined use of soy phytoestrogens and Hup A, estrogens and Hup A, or soy phytoestrogens, estrogen, and Hup A will result in an increase in acetylcholine synthesis and a reduction in the breakdown of acetylcholine in the brain. The overall outcome will be a reduction in neurodegeneration and higher levels of acetylcholine levels in the brain, thereby producing a better cholinergic status for the affected individuals (see FIG. 6). Additionally, the combined use of soy phytoestrogens and estrogen may reduce the necessary dosage for estrogen which, in turn, would reduce the adverse effects of estrogen on the breast and uterus.

All references referred to herein are hereby incorporated by reference in their entirety.

It should be understood that various changes and modifications to the presently preferred embodiments described herein will be apparent to those skilled in the art. Such changes and modifications can be made without departing from the spirit and scope of the present invention and without diminishing its attendant advantages. It is, therefore, intended that such changes and modifications be covered by the appended claims.

What is claimed is:

1. A soy-derived material in combination with Huperzine A in an amount sufficient to improve memory and concentration, wherein the amount of the soy-derived material is about 0.01 mg to about 1000 mg and the amount of Huperzine A is about 0.01 rag to about 150 mg.

2. The combination according to claim 1, wherein the soy-derived material comprises at least one phytoestrogen.

3. The combination according to claim 2, wherein the phytoestrogen is an isoflavone, coumestan, lignan, or any combination thereof.

4. The combination according to claim 3 wherein the phytoestrogenic isoflavone is selected from at least one of genistein, daidzein, biochanin A, formononetin, lo glycitein, the natural glycosides, or metabolites thereof.

5. The combination according to claim 2, wherein the phytoestrogen is extracted from soy, clover, legumes, kudzu root, oilseeds, or any other phytoestrogen containing plant, or chemically synthesized.

6. The combination according to claim 1, wherein the combination is in a dosage form selected from the group consisting of a pill, capsule, tablet, powder, beverage, suspension, emulsion, syrup, solution, patch, and gel.

7. The combination according to claim 1, further including acceptable carriers, diluents, stablizers, solubilizers, lubricants, binders, or excipients thereof.

8. The combination according to claim 1, wherein the mammals include normal cycling pre-perimenopausal women, menopausal women, post-menopausal women, and those suffering with or at risk of developing memory impairment.

\* \* \* \* \*